United States Patent
Papas et al.

(10) Patent No.: US 7,790,190 B2
(45) Date of Patent: Sep. 7, 2010

(54) AQUEOUS EMULSIONS OF LIPOPHILE SOLUBILIZED WITH VITAMIN E TPGS AND LINOLEIC ACID

(75) Inventors: Andreas M. Papas, Kingsport, TN (US); Konstantinos A. Papas, Jonesborough, TN (US); Howard K. Hobbs, Kingsport, TN (US); Warren Hopkins, Kingsport, TN (US); William A. Clark, Johnson City, TN (US)

(73) Assignee: Yasoo Health, Inc., Johnson City, TN (US)

( * ) Notice: Subject to any disclaimer, the term of this patent is extended or adjusted under 35 U.S.C. 154(b) by 919 days.

(21) Appl. No.: 10/805,122

(22) Filed: Mar. 20, 2004

(65) Prior Publication Data

US 2005/0208082 A1 Sep. 22, 2005

(51) Int. Cl.
*A61K 9/00* (2006.01)
(52) U.S. Cl. .................................................. 424/400
(58) Field of Classification Search .................. None
See application file for complete search history.

(56) References Cited

U.S. PATENT DOCUMENTS

| | | | |
|---|---|---|---|
| 3,102,078 A | 8/1963 | Robeson | |
| 4,289,638 A * | 9/1981 | Svenson | 510/258 |
| 5,234,695 A | 8/1993 | Hobbs | |
| 5,626,849 A | 5/1997 | Hastings | |
| 5,824,638 A * | 10/1998 | Burnside et al. | 514/3 |
| 5,883,103 A * | 3/1999 | Burnside et al. | 514/263.38 |
| 5,891,469 A | 4/1999 | Amselem | |
| 6,045,826 A | 4/2000 | Borowy-Borowski | |
| 6,069,167 A | 5/2000 | Sokol | |
| 6,191,172 B1 | 2/2001 | Borowy-Borowski | |
| 6,632,457 B1 | 10/2003 | Sawhney | |
| 6,645,535 B2 | 11/2003 | Zyck | |

FOREIGN PATENT DOCUMENTS

| | | | |
|---|---|---|---|
| WO | WO 96/17626 | | 6/1996 |
| WO | WO 99/29300 | * | 6/1999 |

OTHER PUBLICATIONS

Roy et al., "Vitamin E sensitive genes in the developing rat fetal brain: a high-density oligonucleotide microarray analysis" Oct. 23, 2002; 530(1-3): 17-23.*

* cited by examiner

*Primary Examiner*—Eric E. Silverman

(57) ABSTRACT

Disclosed herein is an aqueous emulsion. The lipid phase of the emulsion includes a blend of a therapeutically effective concentration of a lipophile, a concentration of Vitamin E TPGS, and a concentration of linoleic acid. The presence of linoleic acid increases the solubilizing affect of Vitamin E TPGS on the lipophile and thus reduces the amount of Vitamin E TPGS that would otherwise be required in the aqueous emulsion.

13 Claims, No Drawings

AQUEOUS EMULSIONS OF LIPOPHILE SOLUBILIZED WITH VITAMIN E TPGS AND LINOLEIC ACID

CROSS REFERENCES TO RELATED APPLICATIONS none.

FIELD OF THE INVENTION

The present invention pertains to aqueous emulsions of lipophilic compounds. More particularly, the present invention pertains to improving the solubilization of a lipophile using TPGS as the solubilizing agent.

BACKGROUND OF THE INVENTION

Oral delivery of oily, water-insoluble nutraceutical compounds such as vitamin E is problematic due to the fact that such lipophiles are not well absorbed by the gastrointestinal tract. Oral supplementation of nutraceuticals is particularly problematic for patients having malabsorption conditions. Researchers have found that water-solubilized lipophilic compounds are more readily absorbed by the gastrointestinal tract.

A desirable oral dosage form for administering water-solubilized lipophiles is an aqueous oil-in-water emulsion, especially where patients have difficulty swallowing tablets and capsules. In such systems, the lipophile is solubilized and dispersed throughout the aqueous phase via a solubilizing agent. However, in order to maintain stability so that the lipophilic dispersed phase remains homogeneously distributed throughout the aqueous continuous phase of the emulsion, it is necessary to limit the amount of the solubilized active lipophile in the emulsion to a relatively low concentration. Thus, an undesirably large dosage size would be necessary to deliver an effective amount of nutraceutical lipophile. Moreover, this low "loading" limitation also limits the ability of formulations to include a complex blend of different lipophiles at a reasonable potency. For example, the low loading limitation has precluded a commercially acceptable formulation of an aqueous emulsion containing a blend of all eight homologs of natural source vitamin E because the dosage size would be larger than the acceptable amount of less than about 4 teaspoons (20 mL). Thus, it should be appreciated that it is imperative to use a very effective solubilizing agent in an oil-in-water emulsion. Formulators have found that Vitamin E TPGS is a particularly desirable solubilizing agent. Vitamin E TPGS is a water-soluble form of natural-source vitamin E prepared by esterifying d-alpha-tocopheryl acid succinate with polyethylene glycol 1000. Vitamin E TPGS is a well known compound having a chemical formula of $C_{33}O_5H_{54}$ $(CH_2CH_2O)_n$, where "n" represents the number of polyethylene oxide moieties attached to the acid group of crystalline d-alpha tocopheryl acid succinate. Vitamin E TPGS is hereinafter referred to as simply "TPGS" for convenience.

The tocopherol portion of TPGS is nutraceutically active as a vitamin E source. Thus, the inclusion of TPGS in an aqueous formulation of a lipophile yields the dual functions of providing additional dietary vitamin E and providing solubilization of the lipophile.

While greater amounts of TPGS generally provide more solubilization of the lipophile, TPGS is a relatively expensive material. Yet another critical limiting factor controlling the maximum amount of TPGS in an aqueous emulsion is the fact that the administration of an excess amount of vitamin E, regardless of the source, can overdose a patient with vitamin E. Thus, the nutraceutical potency of an aqueous emulsion of lipophile is further limited by these additional limitations on the amount of TPGS as solubilizing agent.

In light of the above, it is an object of the present invention to provide an aqueous TPGS-solubilized emulsion of a lipophilic nutraceutical that overcomes the above limitations. It is a further object of the present invention to provide a stable aqueous emulsion delivering a higher potency of active nutraceutical lipophile. It is a still further object of the present invention to provide a higher potency aqueous emulsion having a solubilized blend of a higher number of different lipophiles at a higher concentration level than has previously been attainable, with an effective blend of the eight vitamin E homologs being a particularly desired object of this invention. Lastly, it is an object of the present invention that the aqueous emulsion provided be sufficiently concentrated so that an effective amount of lipophilic nutraceutical is delivered in a dosage size no greater than about 4 teaspoons (20 mL).

BRIEF SUMMARY OF THE INVENTION

One aspect of the present invention is an aqueous emulsion wherein the dispersed lipid phase of the emulsion includes a blend of a therapeutically effective concentration of a lipophile, a concentration of TPGS, and a concentration of linoleic acid. The concentration of TPGS and linoleic acid are sufficient for solubilizing the lipophile in the aqueous phase so that the emulsion is stable. Another aspect of the present invention is a solubilizing composition comprising a mixture of TPGS and linoleic acid. The invention also includes a method of treating a patient having a deficiency in a lipophile or otherwise having a condition improved by the administration of a lipophile with the present aqueous emulsion.

DETAILED DESCRIPTION

In the present invention, the inventors have found that, in an aqueous emulsion of a lipophile solubilized with TPGS, the solubilizing ability of TPGS is improved by the presence of linoleic acid. Thus, the amount of TPGS required for solubilizing a given amount of lipophile in water is decreased as compared to a similar emulsion having an absence of linoleic acid. Since linoleic acid is a free fatty acid and free fatty acids are classified as lipophiles themselves, one would expect that the addition of linoleic acid to an aqueous emulsion of a therapeutically effective amount of a lipophile (other than linoleic acid) would require an additional amount of TPGS. However, the inventors were surprised to find that the presence of linoleic acid actually improves the solubilization ability of TPGS. It is poignant to note that the substitution of linoleic acid with other free fatty acids, triglycerides, and monoglycerides such as palmitic acid, stearic acid, oleic acid, soy oil, corn oil, canola oil, docosahexanoic acid in the present emulsion negatively affects the solubilization, forming a less stable emulsion. Although the emulsion dynamics are not known by the inventors, it appears that the linoleic acid migrates to the outer area of the micelle and acts as a co-emulsifier with TPGS instead of being encapsulated along with the therapeutically active lipophile. For the purpose of clarity, the term "lipophile" as used herein will refer to lipophilic compounds other than linoleic acid, unless otherwise specified.

The useful concentration range of linoleic acid in the present emulsion is quite broad and ranges from essentially a mere presence of linoleic acid to a higher concentration that is still well below a nutraceutical supplementing dosage, to a much higher concentration that provides an amount of linoleic acid well above a nutraceutical supplementing dosage of linoleic acid. For purposes of the present invention, a "therapeutically effective amount of linoleic acid" is defined herein to include concentrations that would provide a dietary maintenance supplementing dosage, improve linoleic acid deficiency conditions, as well as concentrations that would provide measurable improvement of medical conditions otherwise improved by the administration of linoleic acid. As a benchmark, a daily dietary maintenance supplementing amount of linoleic acid is typically considered to be about 500 mg to about 6 grams, and is commonly provided via oral administration of 1 to 6 softgels containing 500 to 1,000 mg of linoleic acid. Thus, an emulsion having lower level linoleic acid should contain less than 500 mg per daily dose.

The aqueous emulsion of the present invention has an aqueous phase and a lipid phase dispersed throughout the aqueous phase. The lipid phase includes a blend of a therapeutically effective concentration of a lipophile, a concentration of TPGS, and a concentration of linoleic acid. The concentration of TPGS and the concentration of linoleic acid is sufficient for solubilizing the lipophile. The invention also includes a solubilizing composition of TPGS and linoleic acid at corresponding concentrations having the same concentration ratio of TPGS to linoleic acid as is useful in the emulsion.

The lipid phase of the emulsion includes a blend of therapeutically effective amount of the lipophile and a concentration of TPGS and linoleic acid having a weight ratio of from about 10,000:1 to about 1:6 TPGS to linoleic acid. A low concentration of linoleic acid is useful in emulsions where it is not desirable to administer a therapeutically effective "dosing level" of linoleic acid to the patient. Thus, an emulsion wherein the TPGS and linoleic acid are present at a weight ratio from about 10,000:1 to about 10:1 TPGS to linoleic acid, preferably about 1,000:1 to about 100:1 TPGS to linoleic acid, is a useful aspect of the invention. In applications where a higher presence of linoleic acid is not contraindicated in the patient's diet, an emulsion wherein the TPGS and linoleic acid are present at a weight ratio from less than about 10:1 to about 1:6 TPGS to linoleic acid is useful, preferably a weight ratio between about 1:1 to about 1:4 TPGS to linoleic acid.

The therapeutically effective lipophile of the emulsion can be any therapeutically effective lipophilic compound since TPGS solubilizes essentially any lipophilic compound. Examples of particularly useful lipophiles in the present invention includes lipophilic vitamins, coenzyme Q10, carotenoids, alpha-lipoic acid, essential fatty acids (other than linoleic acid), with vitamin E being particularly useful. The TPGS/linoleic acid solubilizing composition of the present invention is particularly useful in allowing for a higher potency aqueous emulsion having a solubilized blend of a higher number of different lipophiles at a higher concentration level than has previously been attainable.

The present invention includes an aqueous emulsion wherein the therapeutically effective lipophile is a mixture of vitamin E homologs. The eight vitamin E homologs are alpha-tocopherol, beta-tocopherol, gamma-tocopherol, delta-tocopherol, alpha-tocotrienol, beta-tocotrienol, gamma-tocotrienol, and delta-tocotrienol. An aqueous emulsion containing an acceptably high concentration of each of the eight vitamin E homologs to provide a product administrable at an acceptably low oral dosage size is provided. For example, a 1-mL dose of a mixed vitamin E formulation of the present emulsion preferably includes about 25 to about 50 mg vitamin E, higher levels than have previously been deliverable in the same amount of emulsion. This high dose vitamin E formulation preferably includes each homolog. A preferable dosing mixture has a concentration of about 25 to about 50 weight percent alpha-tocopherol, about 0.1 to about 5 weight percent beta-tocopherol, about 25 to about 50 weight percent gamma-tocopherol, about 5 to about 25 weight percent delta-tocopherol, about 0.1 to about 5 weight percent alpha-tocotrienol, about 0.1 to about 5 weight percent beta-tocotrienol, about 0.1 to about 5 weight percent gamma-tocotrienol, and about 0.1 to about 5 weight percent delta-tocotrienol.

The aqueous phase of the emulsion is preferably about 80 to about 99 weight percent, more preferably about 85 to 95 weight percent of the emulsion, with the remaining portion being the lipid phase described above. The aqueous emulsion of the present invention is preferably made by melt blending the lipophile, TPGS, and linoleic acid; contacting the lipid blend with water to form about an 80 to about a 99 weight percent aqueous mixture; and intimately mixing the mixture for a period of time to provide an emulsion that is stable at room temperature (at least 20 days). The lipid blend preferably includes a concentration of from about 10 to about 75 weight percent of the therapeutically effective lipophile, a concentration of from about 10 to about 75 weight percent TPGS, and a concentration of from about 0.01 to about 50 weight percent linoleic acid.

The invention includes oral dosage forms such as an oral emulsion and an emulsion-filled capsule. Topical dosage forms of the present emulsion such as creams and ointments are included.

The invention further includes a method of treating a patient having a deficiency of a lipophile or otherwise having a condition that is improved by the administration of a lipophile to the patient. Examples of such conditions include dietary deficiencies, malabsorption conditions, nutrient depleting diseases, and various other conditions that are improved by increased amounts of a lipophile. A "therapeutically effective amount" of lipophile in treating such a condition is an amount that shows a measurable improvement in the condition. Treatment comprises administering to the patient an aqueous emulsion of the present invention wherein the lipophile is a lipophilic compound other than linoleic acid. In the preferred embodiment of the present invention, the lipophile is a vitamin E blend and an oral emulsion is administered to treat a vitamin E malabsorption condition.

This invention can be further illustrated by the following examples. It will be understood that these examples are included merely for purposes of illustration and are not intended to limit the scope of the invention.

EXAMPLES

The following commercially available compounds were used in the examples:
1. MTS-70 vitamin E, a blend of natural-source vitamin E homologs, available from the Archer Daniels Midland Company.
2. Vitamin E TPGS, from Eastman Chemical Company.
3. Linoleic acid 55%, from Fluka Chemika.
4. MYVEROL 18-99, monoglyceride from Eastman Chemical Company, a known emulsifier characterized by 61% glycerol monooleate (C:18-1), 21% glycerol monolinoleate (C:18-2).
5. USP grade propylene glycol from Dow Chemical Company.
6. Palmitic acid 90%, from Aldrich.
7. Stearic acid 95%, from Aldrich.
8. Oleic acid 90%, from Aldrich.

9. Soy oil, 100% food grade soybean oil.
10. Corn oil, 100% food grade corn oil.
11. Canola oil, 100% food grade canola oil.
12. 40% docosahexanoic acid in Algal vegetable oil (algal oil, high oleic sunflower oil, tocopherols and ascorbyl palmitate as antioxidant).
13. Sorbic acid 100%, from Hoescht.

The homogenizer equipment used was an Avestin Emulsiflex C-5.

In each of the examples, stability of the emulsions was determined via visual inspection of the samples at room temperature after homogenation of the lipid portion with the aqueous portion. The samples were considered as being "stable" if the mixture remained in a dispersed emulsion without separating into two distinct phases for at least 20 days.

Example 1

20% Wt Lipids in Water

In each of Samples 1-4, an amount of MTS-70 vitamin E and an amount of TPGS totaling 40 grams was melt blended together to 50° C. forming a lipid portion. In a separate vessel, 160 grams water (with 0.2 grams potassium sorbate added as antimicrobial agent) was heated to 50° C. The lipid portion and water were combined and stirred while cooled. The mixture was then homogenized at 7,000 to 8,000 rpm.

Table 1 shows that the thus formed aqueous emulsion of 20 percent weight lipid solids failed to maintain stability at room temperature unless the ratio of TPGS to MTS-70 vitamin E is greater than about 10:1.

Table 1 further shows that a greater amount of TPGS is required to solubilize a greater amount of lipophile in water.

TABLE 1

| Sample | Vit E % wt/wt | TPGS % wt/wt | Water % wt/wt | Stability |
| --- | --- | --- | --- | --- |
| 1 | 4.0 | 16.0 | 80.0 | unstable |
| 2 | 3.0 | 17.0 | 80.0 | unstable |
| 3 | 2.2 | 17.8 | 80.0 | unstable |
| 4 | 1.6 (3.2 g) | 18.4 (36.8 g) | 80.0 (180 g) | stable |

Example 2

10% Wt Lipids in Water

Emulsions of MTS-70 vitamin E, TPGS, and water were made according to Example 1, except that the lipids content was reduced to 10 weight percent. An amount of 0.15 grams sorbic acid was added to each 200 gram sample as an antimicrobial.

The data in Table 2 for Samples 5-13 show that, in an aqueous emulsion of 10 weight percent lipids, the ratio of TPGS to MTS-70 vitamin E at room temperature must be at least about 4:1.

The 200 gram stable Sample 6 was loaded with 4 grams MTS-70 vitamin E to provide an overall lipid load of 4 grams MTS-70 vitamin E and 16 grams TPGS per 200 grams of emulsion.

TABLE 2

| Sample | Vit E % wt/wt | TPGS % wt/wt | Water % wt/wt | Stability |
| --- | --- | --- | --- | --- |
| 5 | 1.0 | 9.0 | 90.0 | stable |
| 6 | 2.0 (4.0 g) | 8.0 (16.0 g) | 90.0 | stable |
| 7 | 3.0 | 7.0 | 90.0 | unstable |
| 8 | 4.0 | 6.0 | 90.0 | unstable |
| 9 | 5.0 | 5.0 | 90.0 | unstable |
| 10 | 6.0 | 4.0 | 90.0 | unstable |
| 11 | 7.0 | 3.0 | 90.0 | unstable |
| 12 | 8.0 | 2.0 | 90.0 | unstable |
| 13 | 9.0 | 1.0 | 90.0 | unstable |

Example 3

10% Lipids in Water with Linoleic Acid

In Samples 14-31 linoleic acid was added to the lipid portion of the emulsion prior to melt blending the lipid portion. In each sample, a total of 20 grams MTS-70 vitamin E, TPGS, and linoleic acid were melt blended as in Example 1 and combined with 180 grams water to provide an aqueous emulsion of 10 weight percent lipids. An amount of 0.15 grams sorbic acid was added as an antimicrobial. The mixture was homogenized at 5,000 rpm, then further at 22,000 rpm.

TABLE 3

| Sample | Vit E (% wt) | TPGS (% wt) | Linoleic Acid (% wt) | Water (% wt) | Stability |
| --- | --- | --- | --- | --- | --- |
| 14 | 3.0 (6 g) | 7.0 | 0 | 90.0 | unstable |
| 15 | 3.0 | 6.0 | 1.0 | 90.0 | unstable |
| 16 | 3.0 | 5.0 | 2.0 | 90.0 | stable |
| 17 | 3.0 | 4.0 | 3.0 | 90.0 | stable |
| 18 | 3.0 | 3.0 | 4.0 | 90.0 | stable |
| 19 | 3.0 | 2.0 | 5.0 | 90.0 | stable |
| 20 | 3.0 | 1.0 | 6.0 | 90.0 | stable |
| 21 | 3.0 | 0.5 | 6.5 | 90.0 | failed |
| 22 | 3.0 | 0 | 7.0 | 90.0 | failed |
| 23 | 6.0 (12 g) | 4.0 | 0 | 90.0 | unstable |
| 24 | 6.0 | 3.5 | 0.5 | 90.0 | unstable |
| 25 | 6.0 | 3.0 | 1.0 | 90.0 | stable |
| 26 | 6.0 | 2.5 | 1.5 | 90.0 | stable |
| 27 | 6.0 | 2.0 | 2.0 | 90.0 | stable |
| 28 | 6.0 (12 g) | 1.5 (3 g) | 2.5 (5 g) | 90.0 | stable |
| 29 | 6.0 | 1.0 | 3.0 | 90.0 | unstable |
| 30 | 6.0 | 0.5 | 3.5 | 90.0 | failed |
| 31 | 6.0 | 0 | 4.0 | 90.0 | failed |

Table 3 shows that the addition of linoleic acid to the lipid portion did not necessitate the use of a greater amount of TPGS for stability of the emulsion, as was expected for a fatty acid. Instead, it can be seen that the addition of linoleic acid to the lipid portion reduced the amount of TPGS needed for stabilizing the dispersion of the lipid portion in the water.

It can be seen that Sample 28 had a load of 12 grams MTS-70 vitamin E, 3 grams TPGS, and 5 grams linoleic acid in a 200 gram sample of the emulsion. This is a significant improvement when compared to Examples 1 and 2 where linoleic acid was not used. Note that the stable aqueous emulsion of 10 weight percent lipids in Sample 6 provided a 4 gram load of MTS-70 vitamin E and 16 grams TPGS in a 200 gram sample of emulsion. Thus, the use of linoleic acid in the lipid portion provided a three-fold increase in the MTS-70 vitamin E loading ability (from 4 grams to 12 grams) and greater than a five-fold decrease in the amount of TPGS required (from 16 grams to 3 grams).

Example 4

TPGS/Linoleic Acid in Water with No Lipophile

Various ratios of TPGS and linoleic acid were melt blended together with no other therapeutically active lipophile and then combined and homogenized with water to provide emulsions having a 10 weight percent lipid solids content. Samples 32-43 shown in Table 4 illustrate that a synergistic emulsifying relationship exists between TPGS and linoleic acid in water.

Without being bound to theory, when comparing this Example 4 to Example 2, it appears that linoleic acid acts as a co-emulsifier with TPGS in water instead of being dissolved within the dispersed TPGS-solubilized lipid micelles like MTS-70 vitamin E as well as other typical lipophiles. Thus, the presence of linoleic acid in the aqueous emulsion reduces the amount of TPGS required to solubilize the lipophile. As a result, a smaller amount of TPGS is required to provide the same degree of solubilization of the lipophile.

TABLE 4

| Sample | TPGS % wt/wt | Linoleic A. % wt/wt | Water % wt/wt | Stability |
|---|---|---|---|---|
| 32 | 10.0 | 0 | 90.0 | stable |
| 33 | 9.5 | 0.5 | 90.0 | stable |
| 34 | 9.0 | 1.0 | 90.0 | stable |
| 35 | 8.0 | 2.0 | 90.0 | stable |
| 36 | 7.0 | 3.0 | 90.0 | stable |
| 37 | 6.0 | 4.0 | 90.0 | stable |
| 38 | 5.0 | 5.0 | 90.0 | stable |
| 39 | 4.0 | 6.0 | 90.0 | stable |
| 40 | 3.0 | 7.0 | 90.0 | stable |
| 41 | 2.0 | 8.0 | 90.0 | stable |
| 42 | 1.0 | 9.0 | 90.0 | stable |
| 43 | 0.0 | 10.0 | 90.0 | failed |

Example 5 (Comparison)

Linoleic Acid in Water (No TPGS)

In samples 44 through 55, mixtures of linoleic acid in 100% to 90.0% weight water were prepared for comparison against Example 4.

For each sample, the water was heated to 80° C., the linoleic acid was heated to 50° C., then the acid and water were mixed together until cool. As shown in Table 5, each sample separated instantly without ever achieving emulsification. Thus, each sample failed instantly. Linoleic acid does not appear to have an emulsifying effect in water in the absence of TPGS.

TABLE 5

| Sample | Linoleic A. % wt/wt | Water % wt/wt | Stability |
|---|---|---|---|
| 44 | 0 | 100.0 | failed instantly |
| 45 | 0.5 | 99.5 | failed instantly |
| 46 | 1.0 | 99.0 | failed instantly |
| 47 | 2.0 | 98.0 | failed instantly |
| 48 | 3.0 | 97.0 | failed instantly |
| 49 | 4.0 | 96.0 | failed instantly |
| 50 | 5.0 | 95.0 | failed instantly |

TABLE 5-continued

| Sample | Linoleic A. % wt/wt | Water % wt/wt | Stability |
|---|---|---|---|
| 51 | 6.0 | 94.0 | failed instantly |
| 52 | 7.0 | 93.0 | failed instantly |
| 53 | 8.0 | 92.0 | failed instantly |
| 54 | 9.0 | 91.0 | failed instantly |
| 55 | 10.0 | 90.0 | failed instantly |

Example 6 (Comparison)

Linoleic Acid and Lipophile in Water (No TPGS)

In samples 56 through 67, mixtures of linoleic acid, MTS-70 vitamin E, and water were prepared for comparison to Example 3.

For each sample, the water was heated to 80° C., the linoleic acid and MTS-70 vitamin E were melt blended to 50° C., then the lipophiles and water were mixed together until cool. As shown in Table 6, all samples separated instantly without ever forming an emulsion. Thus, linoleic acid did not solubilize the MTS-70 vitamin E in the absence of TPGS. By analyzing Examples 3, 5, and 6 together, it is clear that a synergistic relationship exists between TPGS and linoleic acid in an aqueous system.

TABLE 6

| Sample | Vit E (% wt) | Linoleic Acid (% wt) | Water (% wt) | Stability |
|---|---|---|---|---|
| 56 | 10.0 | 0 | 90.0 | failed instantly |
| 57 | 9.5 | 0.5 | 90.0 | failed instantly |
| 58 | 9.0 | 1.0 | 90.0 | failed instantly |
| 59 | 8.0 | 2.0 | 90.0 | failed instantly |
| 60 | 7.0 | 3.0 | 90.0 | failed instantly |
| 61 | 6.0 | 4.0 | 90.0 | failed instantly |
| 62 | 5.0 | 5.0 | 90.0 | failed instantly |
| 63 | 4.0 | 6.0 | 90.0 | failed instantly |
| 64 | 3.0 | 7.0 | 90.0 | failed instantly |
| 65 | 2.0 | 8.0 | 90.0 | failed instantly |
| 66 | 1.0 | 9.0 | 90.0 | failed instantly |
| 67 | 0 | 10.0 | 90.0 | failed instantly |

Example 7 (Comparison)

Other Fatty Acids and Emulsifier

A series of nine different sets of comparison samples of aqueous emulsions of 10 weight percent lipids were prepared using other free fatty acids, triglycerides, monoglycerides. The samples were prepared following the methodology and concentrations shown in Example 3, except that linoleic acid was replaced with a different compound for each set of samples prepared. The substitute compounds were propylene glycol (mild emulsifier), palmitic acid, stearic acid, oleic acid, soy oil, corn oil, canola oil, docosahexanoic acid (in Algal vegetable oil), and MYVEROL 18-99 monoglyceride, known to be a good emulsifier. None of these other lipophilic compounds provided stable emulsions with TPGS and vitamin E in an aqueous emulsion of 10 weight percent lipids. Thus, the synergistic relationship found to exist between TPGS and linoleic acid does not exist between TPGS and the similar compounds compared in this example.

In light of the Examples shown above, it is clear that the synergistic relationship between TPGS and linoleic acid in improving solubilization of a therapeutically effective lipophile in water is significant and unexpected.

The invention has been described in detail with particular reference to preferred embodiments thereof, but it will be understood that variations and modifications can be effected within the spirit and scope of the invention.

The invention claimed is:

1. An oil-in-water emulsion consisting of an aqueous phase and a lipid phase dispersed throughout said aqueous phase, said lipid phase consisting of
    a) a therapeutically effective amount of a lipophile chosen from among the group consisting of lipophilic vitamins, Coenzyme Q10, carotenoids, alpha-linoleic acid, essential fatty acids, and combinations thereof; and
    b) a solubilizing composition consisting of Vitamin E TPGS and linoleic acid.

2. The emulsion according to claim 1 wherein the aqueous phase is about 80 to about 99 weight percent, and the lipid phase is about 1 to about 20 weight percent, of the emulsion.

3. The emulsion according to claim 1 wherein said Vitamin E TPGS and said linoleic acid are present at a weight ratio between about 10,000:1 to about 1:6 Vitamin E TPGS to linoleic acid.

4. The emulsion according to claim 1 wherein said Vitamin E TPGS and said linoleic acid are present at a weight ratio between about 10,000:1 to about 10:1 Vitamin E TPGS to linoleic acid.

5. The emulsion according to claim 3 wherein said Vitamin E TPGS and said linoleic acid are present at a weight ratio of about 10:1 to about 1:6 Vitamin E TPGS to linoleic acid.

6. The emulsion according to claim 5 wherein said Vitamin E TPGS and said linoleic acid are present at a weight ratio between about 1:1 to about 1:4 Vitamin E TPGS to linoleic acid.

7. The emulsion according to claim 1 wherein said lipophilic vitamins comprise vitamin E homologs selected from the group consisting of alpha-tocopherol, beta-tocopherol, gamma-tocopherol, delta-tocopherol, alpha-tocotrienol, beta-tocotrienol, gamma-tocotrienol, delta-tocotrienol, and combinations thereof.

8. A method of forming the oil-in-water emulsion of claim 1 comprising:
    a) melt blending a mixture of lipids having a concentration of from about 10 to about 75 weight percent of a therapeutically effective lipophile, a concentration of from about 10 to about 75 weight percent Vitamin E TPGS, and a concentration of from about 0.01 to about 50 weight percent linoleic acid to provide a lipid phase wherein the sum of said concentrations equals a total of 100 weight percent;
    b) contacting the lipid phase with an amount of water to form about an 80 to about a 99 weight percent aqueous mixture; and
    c) admixing the mixture for a period of time to provide an emulsion that is stable at room temperature.

9. The method according to claim 8 wherein said lipophile further comprises a mixture of vitamin E homologs selected from the group consisting of alpha-tocopherol, beta-tocopherol, gamma-tocopherol, delta-tocopherol, alpha-tocotrienol, beta-tocotrienol, gamma-tocotrienol, delta-tocotrienol, and a combination thereof.

10. A method of treating a patient comprising administering an oil-in-water emulsion of claim 1 to the patient.

11. The method of claim 10 wherein the lipophilic vitamin is vitamin E.

12. The method of claim 10 wherein said administration is oral administration.

13. The method of claim 10 wherein said administration is topical administration.

* * * * *